United States Patent
Jaramillo De Echeverri

(10) Patent No.: US 11,667,868 B2
(45) Date of Patent: Jun. 6, 2023

(54) METHOD FOR PRODUCING CLARIFIED OIL FROM COFFEE GROUNDS AND FROM WHOLE AND/OR DAMAGED BEANS

(71) Applicant: Carmenza Jaramillo De Echeverri, Manlzales (CO)

(72) Inventor: Carmenza Jaramillo De Echeverri, Manlzales (CO)

( * ) Notice: Subject to any disclaimer, the term of this patent is extended or adjusted under 35 U.S.C. 154(b) by 426 days.

(21) Appl. No.: 16/625,421

(22) PCT Filed: Jun. 6, 2018

(86) PCT No.: PCT/IB2018/054071
§ 371 (c)(1),
(2) Date: Dec. 20, 2019

(87) PCT Pub. No.: WO2018/234914
PCT Pub. Date: Dec. 27, 2018

(65) Prior Publication Data
US 2021/0324296 A1 Oct. 21, 2021

(30) Foreign Application Priority Data
Jun. 21, 2017 (CO) .......................... NC2017/0006176

(51) Int. Cl.
*C11B 1/02* (2006.01)
*A23F 5/16* (2006.01)
*A23F 5/48* (2006.01)
*C11B 1/10* (2006.01)
*C12N 1/14* (2006.01)

(52) U.S. Cl.
CPC .............. *C11B 1/025* (2013.01); *A23F 5/163* (2013.01); *A23F 5/483* (2013.01); *C11B 1/10* (2013.01); *C12N 1/14* (2013.01)

(58) Field of Classification Search
None
See application file for complete search history.

(56) References Cited

U.S. PATENT DOCUMENTS

| | | |
|---|---|---|
| 5,091,089 A | 2/1992 | Shen et al. |
| 6,923,912 B1 | 8/2005 | Bowling et al. |
| 7,201,847 B1 | 4/2007 | Bowling et al. |
| 9,068,171 B2 | 6/2015 | Kelly et al. |
| 2009/0032459 A1 | 2/2009 | Tanabe |
| 2014/0065263 A1 | 3/2014 | Kelly et al. |
| 2015/0257406 A1 | 9/2015 | Kelly et al. |
| 2021/0324296 A1* | 10/2021 | Jaramillo De Echeverri ............. C11B 1/025 |

FOREIGN PATENT DOCUMENTS

| | | |
|---|---|---|
| CN | 103 773 593 B | 1/2015 |
| CN | 105 925 364 A | 9/2016 |
| TW | 201 524 573 A | 7/2015 |

OTHER PUBLICATIONS

Rodriguez, S. et al. Tratamiento De Efluentes Industriales Coloreados Con *Pleurotus* Spp. Rev Iberoam Micol 2003; 20: 164-168. [retrieved on Sep. 29, 2018], Retrieved from <https://www_researchgate.net/publicaton/255636726_Tratamiento_de_efluemes_industriales_coloreados_con_Pleurotus_spp> The whole document.

Garcia-Oduardo, N. et al., Enzimas Lacasa En Inóculos De *Pleurotus* Spp. RTQ vol. 37, No. 1, Santiago de Cube ene.-abr. 2017. ISSN: 2224-6185. [retrieved on Sep. 27, 2018]. Retrieved from <http://scielo.sld.cu/scielo.php?script=sci_arttext&pid=S2224-61852017000100004> The whole document.

Terasawa, N. et al. Decolorization of Brown Pigments in Foods by Immobilized Mycelia of Coriolus Versicolor Info 30340 and Paecilomyces Canadensis NC-1. Journal of Food Science—vol. 65, No. 5, 2000. https://doi.org/10.1111/j.1365-2621.2000.tb13602.x Results and discussions, conclusion.

Lopez, E.M. et al., Extracción De Aceite a Partir De Subproductos De La Trilla De Café Pergamino. Cenicafé, 50 (1):66-77. 1999. [retrieved on Sep. 28, 2018]. Retrieved from <https://.cenicafe.org/es/publications/arc050%2801%29066-077.pdf>The whole document.

Terasawa, N. et al., Isolation of a Fungus to Decolorize Coffee. Biosci. Biotech. Biochem., 58(11),2093-2095, 1994. DOI: 10.1271/bbb.58.2093 The whole document.

Tsioulpas, A. et al., Phenolic removal in olive oil mill wastewater by strains of *Pleurotus* spp. in respect to their phenol oxidase (laccase) activity. Bioresource Technology 84 (2002) 251-257. http://doi.org/10.1016/S0960-8524(02)00043-3 The whole document.

Kissi, M. et al., Roles of two white-rot basidiomycete fungi in decolorisation and detoxification of olive mill waste water. Appl Microbiol Biotechnol (2001) 57:221-226 DOI 10.1007/s002530100712 The whole document.

Salmones, D. et al., Comparative culturing of *Pleurotus* spp. on coffee pulp and wheat straw: biomass production and substrate biodegradation. Bioresource Technology 96 (2005) 537-544. doi:10.1016/j.biortech.2004.06.019 The whole document.

Awad, A. et al., Olive Oil Waste Treatment. Waste Treatment in the Food Processing Industry, 2006, p. 139. [retrieved on Oct. 1, 2018]. Retrieved from <https://edisciplinas.usp.br/pluginfile.php/1898957/mod_folder/content/0/material%20para%20a%20elabora%C3%A7%C3%A3o%20de%20projects/Olive%20Oil%20Waste%20Treatment.pdf?forcedownload=1>The whole document.

International Search Report and Written Opinion dated Oct. 5, 2018 in corresponding International Application No. PCT/IB2018/054071 and its English Translation.

(Continued)

*Primary Examiner* — Hope A Robinson
(74) *Attorney, Agent, or Firm* — Haug Partners LLP

(57) ABSTRACT

A method designed to clarify the coffee oil contained in coffee grounds or in whole and/or damaged coffee beans. The method objective is achieved by starting with inoculation of the coffee grounds or coffee beans with macromycetes especially with white rot fungi, continuing with an incubation, step that allows complete population of the coffee grounds or coffee beans by the fungal mycelium to be achieved, and finishing with steps of drying and extracting the coffee oil. The method disclosed allows colourless or pale yellow coffee oil to be produced, favouring the use thereof in cosmetic and food products, amongst others.

8 Claims, 4 Drawing Sheets

(56) References Cited

OTHER PUBLICATIONS

Job, "Use of coffee spent industry residues for production of *Pleurotus ostreatus* (Jacq.:Fr.) Kummer in solid state fermentation," *Rev. Iberoam. Micol.*, 21: 195-197 (2004).
Barbero et al., "The Flavours of Coffee Grounds: The coffee waste as accelerator of new local businesses," *Management of Technology—Step to Sustainable Production*, Bol, Brac, (Croatia), pp. 1-7, Jun. 11-13, 2014.
Caetano, et al., "Valorization of Coffee Grounds for Biodiesel Production," *Chemical Engineering Transactions*, vol. 26, 267-272 (2012).
Haile, et al., "Investigation of Waste Coffee Ground as a Potential Raw Material for Biodiesel Production," *International Journal of Renewable Energy Research*, vol. 3, No. 4, 854-860 (2013).
Supplementary European Search Report dated Feb. 26, 2021 issued in corresponding European Application No. EP 18 81 9628.

\* cited by examiner

METHOD FOR PRODUCING CLARIFIED OIL FROM COFFEE GROUNDS AND FROM WHOLE AND/OR DAMAGED BEANS

CROSS-REFERENCE TO RELATED APPLICATIONS

This application is the National Stage entry under 35 U.S.C. § 371 of International Application No. PCT/IB2018/054071 filed on Jun. 6, 2018, published on Dec. 27, 2018 under Publication Number WO 2018/234914 A1, which claims the benefit of priority under 35 U.S.C. § 119 of Columbia Patent Application Number NC2017/0006176 filed on Jun. 21, 2017, the entireties of which are herein incorporated by reference.

INVENTION FIELD

The present invention belongs to the field of chemical processes and consists of a process for the extraction of clarified coffee oil from spent coffee grounds or whole and/or deteriorated coffee beans. Such process comprises stages of inoculation and incubation of the spent coffee grounds or the coffee beans with macromycetes, thus achieving to eliminate the typical brown color of the coffee and thus obtain clarified coffee oil.

BACKGROUND OF THE INVESTIGATION

Coffee is one of the most widely consumed beverages worldwide, a fact that parallels the generation of large amounts of waste as a result of the processing and preparation of this beverage. Thus, for example, it is estimated that around six million tons of coffee waste are produced annually worldwide, that is, from that solid brown residue that is obtained after treating the roasted and ground coffee beans with hot water to obtain the coffee beverage, and that is also obtained as a result of the treatment of roasted and ground coffee beans to manufacture industrial soluble coffee.

Such residue of spent coffee grounds, whether industrial, commercial or residential, has historically been discarded in the trash cans or sanitary landfills, or eventually used simply as fuel for boilers or as fertilizer. However, in recent years, various investigations have been carried out to study mechanisms to use them in products or processes of greater added value.

Thus, for example, Daniel Job (Rev. Iberoam Micol 2004; 21; 195-197) studied the use of the spent coffee grounds as a base substrate for the cultivation of *Pleurotus* ostreatus (a fungus widely consumed worldwide), finding that the incorporation into the substrate of up to 55% of spent coffee grounds does not diminish the fructifying capacity nor the performance of the *Pleurotus*, and additionally does not imply the absorption of caffeine by the mycelium.

On her part, Silvia Barbero and Eleonora Fiore (MOTSP 2014, Bol, Brac, (Croatia), 11-13 Jun. 2014. pp. 1-7) have studied the use of coffee waste as a source of wealth, noting that, on the one hand, spent coffee grounds contain caffeine, tannins and polyphenols that can have negative effects on the environment, but also contain minerals, melanoidins, lipids, waxes, lignin, proteins and polysaccharides with an outstanding commercial potential.

Now, one of the components of the spent coffee residue with the greatest commercial potential is coffee oil, since it is contained therein in a high percentage, and has also demonstrated various uses in different technological sectors.

As an example, in recent years, several investigations have been carried out to determine the potential use of such coffee oil for the production of biodiesel (N. Caetano, et al., *Chemical Engineering Transactions,* 2012, Vol. 26, 267-272; M. Haile, et al., *International Journal of Renewable Energy Research,* Vol. 3, No. 4, 2013). Likewise, coffee oil additionally possesses antioxidant, antimicrobial and detergent capacities that give it a marked relevance in commercial terms.

In the state of the art, different methods for the extraction of coffee oil are known. For example, in the patent document CN105925364 (University of Qingdao, China, 2016) a method for extracting coffee oil from coffee beans through ultrasonic waves is disclosed, which comprises the following steps: Drying of coffee beans, uniform mixing of dried coffee beans with an organic solvent to obtain a mixed stock solution, ultrasonic treatment of the stock solution until a mixed solution of coffee oil and organic solvent is obtained, suction filtration, and distillation of the obtained filtrate obtained to recover the organic solvent and obtain coffee oil.

According to the inventors, such method is advantageous for its simplicity, the short extraction time required, the high extraction rate, the low acidity value of the extracted coffee oil, the good quality of the oil, and the minimum energy consumption.

On the other hand, patent document TW201524573 teaches that coffee oil can be extracted efficiently from recycled coffee beans using supercritical extraction with carbon dioxide, thus obtaining a coffee oil characterized for containing one or more unsaturated fatty acids, and because it has antioxidant effects, softening of the skin and absorption of UV rays that make it an excellent cosmetic ingredient. Indeed, according to the inventors, the recycled coffee has a porous structure and has low oil content, being a cosmetic ingredient suitable for all kinds of exfoliating and cleansing cosmetic products. Additionally, it is pointed out that the recycled coffee can be processed using a second extraction step with water to obtain an extract that has an antioxidant effect and is suitable as a cosmetic ingredient.

Despite the above, although today the economic importance of coffee oil is fully recognized, the serious inconvenience continues to be that it presents a dark brown color, a characteristic not desired in foods, soaps, and other cosmetics, and which has therefore been outstanding in limiting its use in this class of commercial sectors.

Given the above, it is clear that in the state of the art, there was still the need to develop a process that would allow the extraction of clarified coffee oil from spent coffee grounds and/or coffee beans, so that such oil could be used as large-scale raw material in the cosmetic and food industries, and in this way provide a high added value to coffee residues.

OVERALL DESCRIPTION OF THE INVENTION

Keeping in mind the serious inconveniences that commercially are generated by the marked brown characteristic of coffee oil,—regardless of its method of extraction, according to the teachings of the prior state of the art—the applicant of the invention in question developed a process for obtaining clarified oil from spent coffee grounds and whole and/or deteriorated coffee beans.

Indeed, the process disclosed here allows to obtain coffee oil which is characterized because it is extracted from spent coffee grounds or recycled coffee beans (that is, from material that to date is mostly discarded or simply used as fuel in boilers), and additionally because such process comprises particular steps that allow the coffee oil to be clarified, in other words, because they allow the extracted oil not to have the typical dark brown color, but to be a transparent oil, or at least slightly yellowish, without this meaning in any way, a loss of its chemical characteristics and therefore of its potential applications.

Basically, the developed process consists of inoculating the spent coffee grounds and/or the coffee beans with macromycetes called white rot fungi, some examples are the following: *Pleurotus* spp., *Corolius versicolor, Lentinula edodes*, among others.

In this sense, such process comprehensively comprises the following stages:

Inoculation of spent coffee grounds and/or coffee beans with macromycetes, particularly white rot fungi;

Incubation of the mixture formed by the spent coffee grounds and/or coffee beans with macromycetes for a sufficient period of time to ensure that the spent coffee waste is completely populated by the mycelium of the fungus;

Drying of the inoculated and completely populated spent coffee grounds; And,

Extraction with solvents of the coffee oil from the dried spent coffee grounds.

This process allows obtaining transparent or slightly yellowish coffee oil.

It is important to note that this process is effective (the discoloration of the oil is achieved in short periods of time and without eliminating its chemical properties), and it is also remarkably simple and economical, allowing an added value of great relevance for the coffee industry.

DETAILED DESCRIPTION OF THE INVENTION

Figure 1:
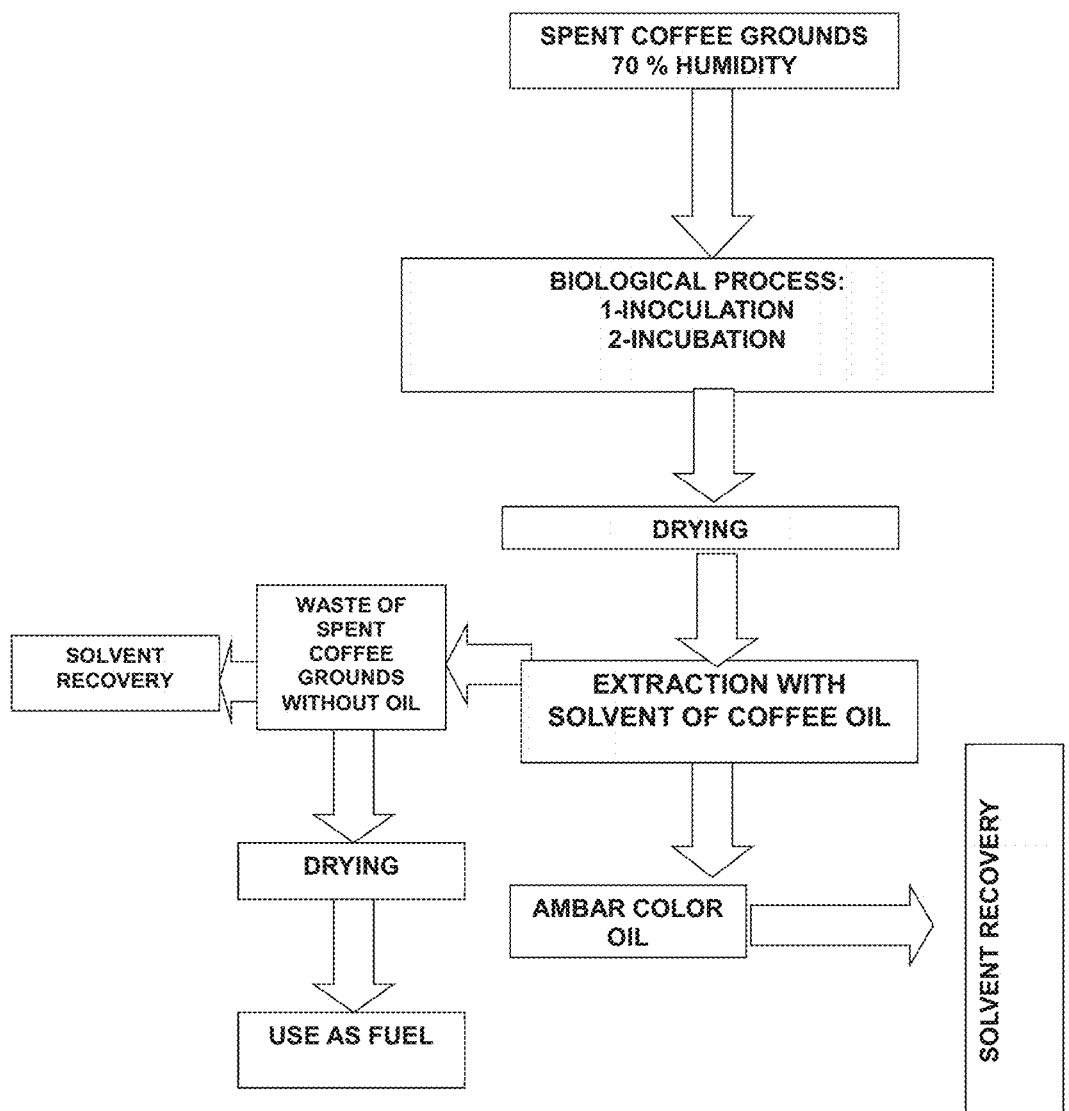
FIG. 1 is a flow chart of the process revealed here, showing the different stages involved and the main laboratory conditions used.
Figure 2:
FIG. 2 is a photograph that allows appreciating a sample of spent coffee grounds inoculated with macromycetes and completely populated, the previous, in accordance with the process here revealed.
Figure 3:
FIG. 3 is a photograph in which the appearance of the previously inoculated and populated spent coffee grounds is observed, and after being subjected to a drying process.

In addition to what was previously stated, the object of the this application can be appreciated in detail by the subsequent description of the stages of the process developed:

The first stage of the process is to carry out the inoculation of the raw material (spent coffee grounds or coffee beans) with macromycetes. Such step involves mixing the raw material with the fungus in such a way that the first one represents between 1% and 10% in wet weight of the mixture, preferably between 2% and 5%.

In a particular realization of the invention, such first stage can be preceded by previous thermal treatments and/or by washing procedures of the raw material. In the case of the spent coffee grounds, the heating of the dough is relevant when it is not fresh, that is, when more than 24 hours have passed since the extraction of the coffee beverage and the respective spent coffee waste has been generated, since the exposure to the environment for more than 24 hours causes the spent coffee waste to fill with fungal spores capable of colonizing the medium very quickly.

On the other hand, when coffee beans are used as raw material, in certain cases it will be advantageous to carry out previous washings with water to remove any impurities from the surface, including fungi that may be growing there, as well as eventually warming the beans to decrease their humidity.

The inoculation can be done with any macromiceate. However, in a preferred model of the invention, the inoculation is carried out with a macromiceate selected from: *Pleurotus* spp., Corolius versicolor, *Lentinula edodes* and mixtures thereof. Micromycetes can also be used, in which case a higher percentage of moisture in the raw material may be required.

The process can be carried out using spent coffee grounds or coffee beans from any variety.

The next step consists in the incubation of the previously obtained mixture, for which generally low-height bins are used (preferably no more than 40 cm tall), which are filled with such mixture and covered with some porous material, for example, surgical fabric.

This incubation process is carried out for 10 to 45 days, time that will depend mainly on the humidity of the mixture and the complete population of the raw material with the fungus.

In a particular model of the invention, the incubation step is carried out at a room temperature close to 30° C., so that the mixture remains at such temperature throughout the incubation period.

The environmental humidity during the incubation period generally ranges between 50 and 60%. However, once the incubation stage is complete, the resulting dough is subjected to drying at a temperature between 35° C. and 55° C. until a final humidity of the material is reached between 5% and 10%.

Finally, the process includes the stage of extraction of the coffee oil by means of solvents and equipment that are fully known and normally used for extraction procedures of chemical compounds. In this sense, this stage starts with the intimate combination of the selected solvent with the dry dough coming from the previous stage, followed by alternating phases of vigorous agitation and rest for a period that can vary between 1 and 3 days. The final phase of distillation and recovery of coffee oil can be carried out with the help of a rotatory evaporator equipment or something similar.

In a particular realization, the solvent used for the extraction is hexane.

EXAMPLE

In order to show the operation and advantages of the process according to this invention, below, we present a comparative example between the extraction of coffee oil through the process disclosed herein and the extraction of coffee oil through a typical mechanism previously known in the state of the art using carbon dioxide.

Used Experimental Conditions

Using bags 60 cm high and 5 meters long with surgical fabric filters every 40 cm, 10 kg of spent coffee grounds from Foodex Manizales, (Company that produces soluble coffee) were inoculated with 0.5 Kg of mycelium of macromycete from the commercial Laboratory of Bogota, Colombia. The incubation process was carried out for a period of 30 days until the complete population of the spent coffee grounds by the mycelium is achieved. Subsequently, such spent coffee grounds were dried in a drying oven at a temperature of 40° C. for 24 hours until achieving a humidity of 10%. Finally, the dry waste was subjected to a commercial Hexane extraction process and the same process used in edible oils.

On the other hand, the experimental conditions necessary to carry out the extraction of edible oils using carbon dioxide gas are described in detail in the literature.

Evaluated Results

Once the extraction processes carried out were completed, the following experimental results were evaluated:

1) Percentage of performance: Amount of coffee oil extracted by each process, divided by the amount of coffee waste used initially and multiplied by one hundred.
2) Color: Visual appearance offered to the naked eye, that is, without using equipment or special mechanisms to determine the color of a fluid.
3) Other organoleptic characteristics: Other physical properties of the coffee oil obtained, including smell, taste, texture, among others.
4) For some calculations the following formulas were used:

Calculation of Humidity:

$$\% H_2O = \frac{PI - PF}{PI} * 100.$$

Calculation of Remaining Humidity:

$$\text{Humid fraction} = \frac{\text{Completely dry sample}}{\text{Humid Sample}}$$

$$\frac{\text{Completely dry sample for experimenting}}{\text{Humid sample for experimenting}} = \text{Humid fraction}$$

$$\text{Ideal water weight} = \text{Humid Sample} - \text{Completely dry sample}$$

$$\text{Actual water weight} = \text{Humid Sample} - \text{Dry sample at } 110° \text{ C.}$$

$$\% \text{Remaining Humid in the Sample} = \frac{\text{Actual water weight}}{\text{Ideal water weight}} * 100\%.$$

Weight of the completely dry spent coffee grounds:

Dry spent coffee=Dry sample−Dry sample*Humidity

Figure 4:
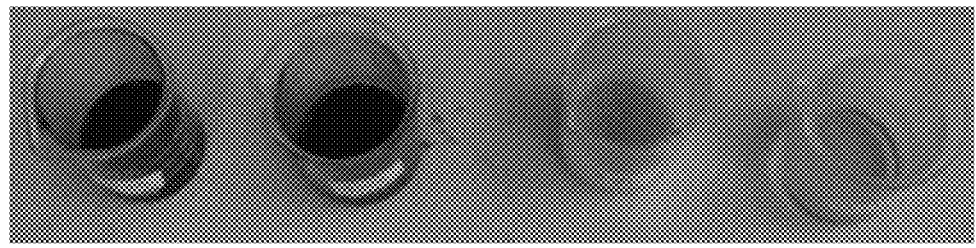
FIG. 4 is a series of photographs that allow us to appreciate: 1) The coffee oil commonly extracted, which is characterized by being dark brown (left); and 2) The clarified coffee oil according to the process disclosed in this invention (right).
Figure 4:
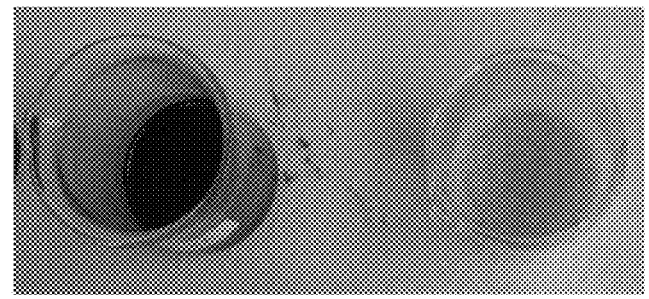

| | Process according to the prior state of the art | Process according to the invention | Additional observations |
|---|---|---|---|
| Performance percentage | 12% | 16.7% | The times correspond to average values |
| Color of the extracted oil. | Dark brown | Transparent/ Slightly yellow | In FIG. 4 the marked difference in the color of the extracted oil is observed |
| Other organoleptic characteristics | Coffee smell | Nutty smell | The flavor of the oil obtained by the process of this invention is similar to that of the almond, with a smooth texture like banana oil. |

From the above, it is possible to say that the extraction process disclosed in this invention allows to effectively eliminate the characteristic brown color of coffee oil from spent coffee grounds or coffee beans, a characteristic that is not achieved with the extraction processes previously known in the state of the art basically because they don't comprise stages of treatment of the raw material (spent coffee grounds or whole or deteriorated coffee beans).

The effective clarification of coffee oil drastically favors its usefulness in the cosmetology, medicinal, personal hygiene and food industries, giving added value to a product commonly treated as waste in the coffee industry.

Additionally, it is pertinent to note that the transparent (or slightly yellowish) coffee oil obtained with the process disclosed here is the result of the treatment of the raw material with macromycetes, but not with the use of chemical products typically used for discoloration processes (for example, hydrogen peroxide and alkaline earth metal chlorides) or the use of very expensive physical processes such as activated carbon filtration.

On the other hand, the performance percentage achieved with the extraction process of this invention (16.7%) ensures the profitability of the process and further demonstrates that such process does not adversely affect the amount of oil obtained.

In fact, the quality of the obtained oil is similar to that of the oils extracted with chemical processes already known in the prior art, but showing serious differences in color and odor, characteristics that broaden the spectrum of use of such coffee oil in different technological sectors, particularly in food and cosmetology.

The invention claimed is:

1. A process for obtaining clarified oil from spent roasted coffee grounds and whole and/or deteriorated roasted coffee beans, wherein the process comprises the following steps:
   a) inoculation of spent roasted coffee grounds and/or whole and/or deteriorated roasted coffee beans with macromycetes comprising white rot fungi having mycelium to form a mixture;
   b) incubation of the mixture until it is completely populated by the mycelium to form an incubated mixture;
   c) drying the incubated mixture; and
   d) solvent extraction of coffee oil from the dried incubated mixture.

2. The process of claim 1, wherein the white rot fungi are selected from *Pleurotus* spp., *Corolius versicolor* and *Lentinula edodes*, or mixtures thereof.

3. The process of claim 1, wherein the spent roasted coffee grounds and/or the whole and/or deteriorated coffee beans comprise between 1% and 10% by wet weight of the mixture.

4. The process of claim 1, wherein the duration of the incubation step is between 10 and 45 days.

5. The process of claim 1, wherein the drying step is performed at a temperature of between 35° C. and 55° C. for a duration of 24 hours.

6. The process of claim 1, wherein the solvent extraction step is performed with a solvent selected from hexane, ethyl acetate or mixtures thereof.

7. The process of claim 1, wherein the spent roasted coffee grounds, undergo thermal treatment by heating prior to inoculation.

8. The process of claim 1, wherein the whole and/or deteriorated coffee beans are washed with water to remove any impurities and thereafter warmed to decrease humidity prior to inoculation.

* * * * *